United States Patent
Kaplan et al.

(10) Patent No.: US 10,874,587 B2
(45) Date of Patent: Dec. 29, 2020

(54) SMART CAPS FOR MEDICATION CONTAINERS

(71) Applicant: WaterIO LTD., Ness Ziona (IL)

(72) Inventors: Nimrod Kaplan, Ness Ziona (IL); Yakov Bentkovski, Ness Ziona (IL)

(73) Assignee: WATERIO LTD., Ness Ziona (IL)

( * ) Notice: Subject to any disclaimer, the term of this patent is extended or adjusted under 35 U.S.C. 154(b) by 214 days.

(21) Appl. No.: 16/302,333

(22) PCT Filed: May 17, 2017

(86) PCT No.: PCT/IL2017/050554
§ 371 (c)(1),
(2) Date: Nov. 16, 2018

(87) PCT Pub. No.: WO2017/199255
PCT Pub. Date: Nov. 23, 2017

(65) Prior Publication Data
US 2019/0298607 A1    Oct. 3, 2019

Related U.S. Application Data

(60) Provisional application No. 62/337,620, filed on May 17, 2016.

(51) Int. Cl.
*A61J 1/03* (2006.01)
*A61J 7/04* (2006.01)
(Continued)

(52) U.S. Cl.
CPC . *A61J 1/03* (2013.01); *A61J 1/00* (2013.01); *A61J 7/04* (2013.01); *A61J 7/0436* (2015.05);
(Continued)

(58) Field of Classification Search
CPC .... A61J 1/03; A61J 7/0436; A61J 1/00; A61J 7/04; A61J 7/02; A61J 7/0427; G08B 21/24; G08B 25/10; G16H 20/10
(Continued)

(56) References Cited

U.S. PATENT DOCUMENTS

| 5,014,798 A | 5/1991 | Glynn |
| 2014/0266760 A1 | 9/2014 | Burke, Jr. et al. |

(Continued)

FOREIGN PATENT DOCUMENTS

WO    WO 2015/200904 A1    12/2015

OTHER PUBLICATIONS

Extended search report for European Patent Application No. EP 17 79 8889, dated Dec. 13, 2019.
(Continued)

*Primary Examiner* — Rafael A Ortiz
(74) *Attorney, Agent, or Firm* — Pearl Cohen Zedek Latzer Baratz LLP

(57) ABSTRACT

A cap for a medication container may include: at least one pressure sensor; an air supplying unit; and a controller. The controller may be configured to: receive a first air pressure measurement form inside the medication container, form the at least one pressure sensor; control the air supply unit to supply air at a predetermined pressure for a predetermined amount of time; receive a second air pressure measurement from inside the medication container, form the at least one pressure sensor; and perform an output operation using the first and second air pressure measurements.

20 Claims, 5 Drawing Sheets

(51) Int. Cl.
  *G08B 21/24* (2006.01)
  *G08B 25/10* (2006.01)
  *A61J 1/00* (2006.01)
  *G16H 20/10* (2018.01)
  *A61J 7/02* (2006.01)
(52) U.S. Cl.
  CPC ............. *G08B 21/24* (2013.01); *G08B 25/10* (2013.01); *A61J 7/02* (2013.01); *G16H 20/10* (2018.01)
(58) Field of Classification Search
  USPC .......... 206/213.1, 530, 823; 220/203.01, 202
  See application file for complete search history.

(56) References Cited

U.S. PATENT DOCUMENTS

| | | | |
|---|---|---|---|
| 2015/0257981 A1* | 9/2015 | Arad | A61J 7/0436 340/573.1 |
| 2016/0239635 A1* | 8/2016 | Fateh | G06F 19/3462 |
| 2018/0184971 A1* | 7/2018 | Hong | A61B 5/02055 |

OTHER PUBLICATIONS

International Search Report of PCT Application No. PCT/IL2017/050554, dated Aug. 30, 2017.

\* cited by examiner

SMART CAPS FOR MEDICATION CONTAINERS

CROSS-REFERENCE TO RELATED APPLICATIONS

This application is a National Phase Application of PCT International Application No. PCT/IL2017/050554, International Filing Date May 17, 2017, claiming benefit of U.S. Provisional Patent Application No. 62/337,620, filed May 17, 2016, which is hereby incorporated by reference.

BACKGROUND OF THE INVENTION

Many people take one or more daily doses of medicines and vitamins in the form of pills, syrup or powder or similar forms to cure temporary ailments, chronic illnesses and pains, or as preventative health measures. Such medicines, dietary supplements and vitamins are typically packaged in pill vials, plastic bottles, or similar containers from which users may dispense the necessary number of pills for their appropriate dosage.

Unlike in a blister pack, where the number of pills already taken from the blister pack is readily evident, vials or bottles do not overtly show how many pills were taken or remain. Currently, patients may track taking a medication from such a container by memory, or by writing down when and how much of the medication was taken. Accordingly, there is a need for an automatic way for tracking the amount of medication left in a container in order to help users to track and control the correct amount of medication or dietary supplements to be taken.

SUMMARY OF THE INVENTION

Some embodiments of the invention may include a cap for a medication container. The cap may include: at least one pressure sensor; an air supplying unit; and a controller. The controller may be configured to: receive a first air pressure measurement form inside the medication container, form the at least one pressure sensor; control the air supply unit to supply air at a predetermined pressure for a predetermined amount of time; receive a second air pressure measurement from inside the medication container, form the at least one pressure sensor; and perform an output operation using the first and second air pressure measurements.

In some embodiments, the controller may further be configured to perform an output operation selected from the group consisting of: sending the received first and second air pressure measurements to an external processor, and determining the amount of medication in the medication container based on the received first and second air pressure measurements, dimensions of the medication container and data related to the type of medication. In some embodiments, the controller may further be configured to: receive dimensions of the medication container; and receive data related to the type of medication inside the medication container.

In some embodiments, the data related to the type of medication may include dimension of pills at which the medication is given such that determining the amount of medication may include determining the number of pills in the medication container. In some embodiments, the data related to the type of medication comprises that the medication is in form of a powder or the medication is in the form of syrup such that determining the amount of medication may include determining the volume of the medication in the container. In some embodiments, the dimensions of the medication are received via a user interface in communication with the controller. In some embodiments, the user interface is at least one of: the user interface included in the cap and a user interface included in a mobile device in communication with the controller.

In some embodiments, the cap may further include an attachment sensor, such that the controller may further be configured to: receive an indication that medication container has been opened and then closed from the attachments sensor; and receive the first air pressure measurement following receiving the indication. In some embodiments, the cap may be adapted to be fitted onto a medication container for storing at least one of the group consisting of: a medical drug, a dietary supplement, infant formula and vitamins.

In some embodiments, the dimensions of the medication container are received from an external controller, and the external controller may further be configured to: receive one or more images of the container from a capturing device; and determine the medication container based on the received one or more images.

In some embodiments, the air supply unit may include at least one of: an air pump and a pressurized air tank.

In some embodiments, the data related to the type of medication may be received via a user interface in communication with the controller. In some embodiments, the data related to the type of medication may be received from an external controller and the external controller may be configured to: receive one or more images of the medication; and determine the data related to the type of medication based on the captured one or more images.

In some embodiments, the controller may further be configured to: present information related to the amount of medication in the medication container one the user interface. In some embodiments, the information related to the amount of medication may include at least one of: the amount of medication; an alert if the amount is below a predetermined level and an alert to take the medication after a predetermined amount of time from a previous reduction in the amount of medication determined by the controller.

In some embodiments, the controller may further be configured to: determine a first amount of medication in the medication container; initiate a time frame for determining a second amount of medication; determine the second amount of medication in the medication container; compare the first amount and the second amount; and send an alert to the user interface based on the result of the comparison.

In some embodiments, the cap may include a communication unit configured to wirelessly communicate with external devices.

Some aspects of the invention may be related to: a computer implemented method of determining the amount of medication in a medication container. Embodiments of the method may include receiving dimensions of the medication container; receiving data related to the type of medication inside the medication container; receiving a first air pressure measurement form inside the medication container, form at least one pressure sensor; controlling an air supply unit to supply air to the container at a predetermined pressure for a predetermined amount of time; receiving a second air pressure measurement from inside the medication container, form the at least one pressure sensor; and determining the amount of medication in the medication container based on the received first and second air pressure measurements, the dimensions of the medication container and the data related to the type of medication.

In some embodiments, the method may further include receiving an indication that medication container has been opened and then closed, form an attachments sensor; and receiving the first air pressure measurement following receiving the indication.

In some embodiments, the method may further include receiving one or more images of the container from a capturing device; and determining the medication container based on the received one or more images.

In some embodiments, the method may further include receiving one or more images of the medication; and determining the data related to the type of medication based on the captured one or more images.

In some embodiments, the method may further include presenting information related to the amount of medication in the medication container on a user interface.

In some embodiments, the method may further include determining a first amount of medication in the medication container; initiating a time frame for determining a second amount of medication; determining the second amount of medication in the medication container; comparing the first amount and the second amount; and sending an alert to the user interface if the comparison yields that the second amount is equal to the first amount or that the second amount is different from a predetermined expected second amount.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
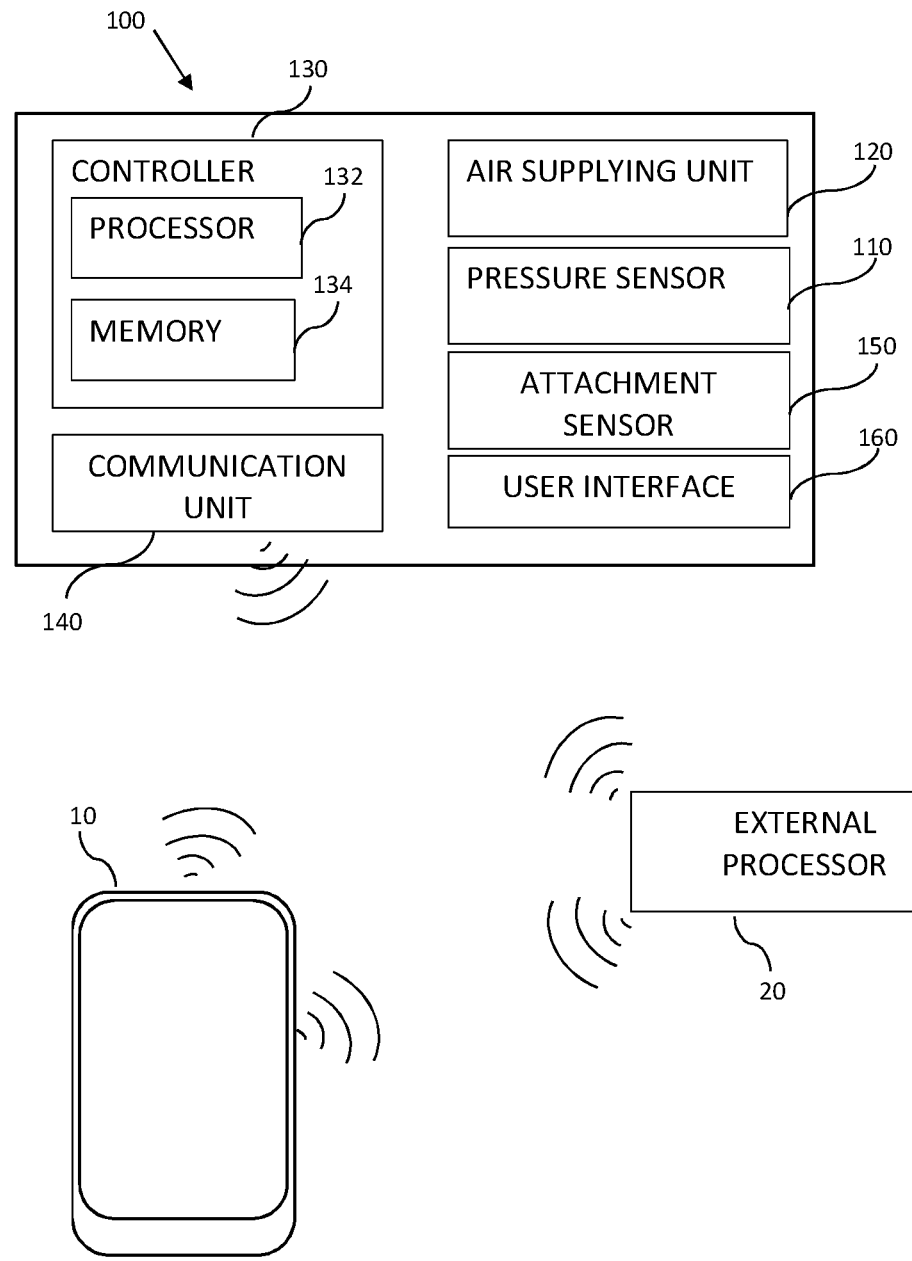
FIG. 1A is a high level block disarm of components included in a cap for a medication container according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some aspects of the invention may be related to a smart cap for a medication container that may present to a user the amount of medication left in the container or an information related to the amount, either on a display attached to the cup or on a screen of mobile device associated with the user. As used herein the term "medication" may be related all types of drugs, dietary supplements (e.g., for athletes, women, elderly people, etc.), infant formula, vitamins etc. to be taken orally. A smart cap according to some embodiments of the invention may be able to follow the consumption of the medication and alert the user if the medication was not taken properly. For example, the smart cap may be able to calculate the number of pills left in the container after the user took one or more pills from the container and then follow the time interval between each reduction in the number of pills (which indicates that at least one pill was taken). If the time interval was longer than a predetermined amount of time or that the number of pills taken is incorrect, the smart cap may be able to send an alert to the user, either to the display included to the cup or to the mobile device associated with the user.

Figure 1B:
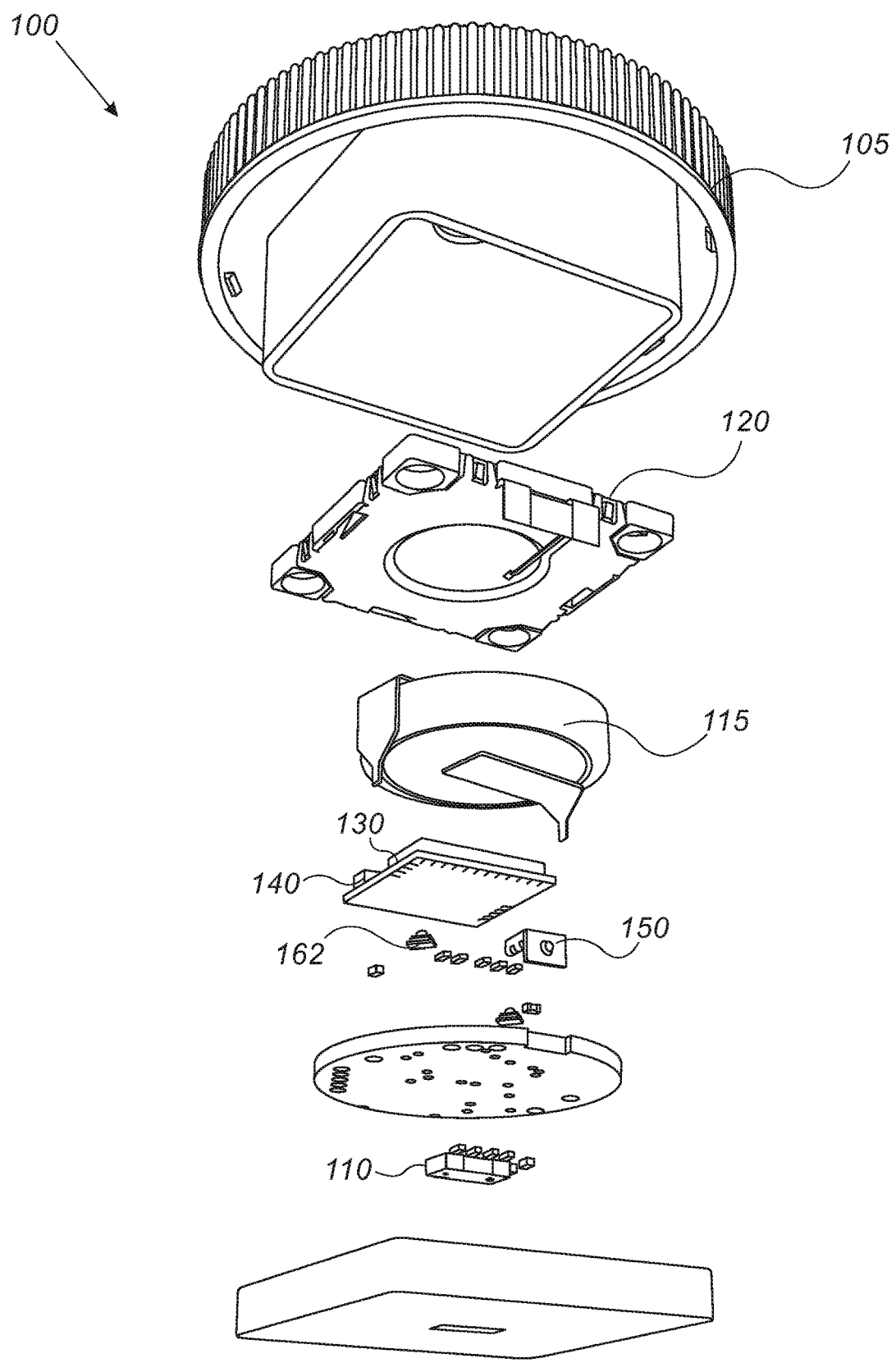
FIG. 1B is an illustration of a cap for a medication container according to some embodiments of the invention.
Figure 1C:
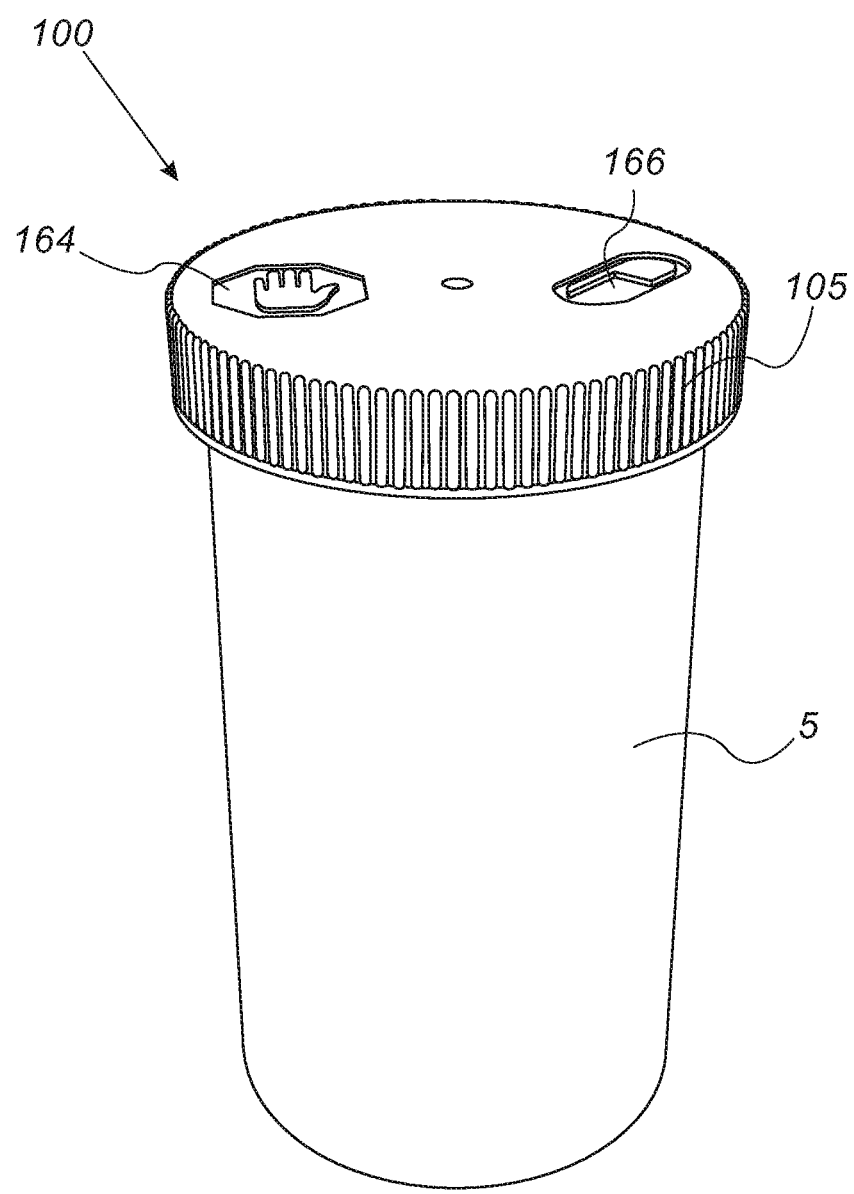
FIG. 1C is an illustration of a container with a cap for a medication container according to some embodiments of the invention.

Reference is now made to FIG. 1, which is a high level block diagram of components included in a cap for a medication container according to some embodiments of the invention. A cap 100 may include at least one pressure sensor 110, an air supplying unit 120 and a controller 130. Cap 100 may further include a cap housing 105 illustrated in FIGS. 1B and 1C. In some embodiments, cap 100 may further include one or more of a communication unit 140, an attachment sensor 150 and a user interface 160. In some embodiments, cap 100 may further include a battery 115 (illustrated in FIG. 1B).

Pressure sensor 110 may be any type of pressure sensor for measuring air pressure in a closed container, for example, a pressure sensor integrated circuit (e.g., BM1383AGLV by ROHM Semiconductors), a microelectronic mechanical sensor (MEMS) nano-pressure sensor (e.g., LPS22HB by ST Microelectronics) or the like.

Air supply unit 120 may include at least one of: an air pump (e.g., low-profile, high-speed and high-pressure air pump (e.g., low-profile, high-speed and high-pressure air pump manufactured by Murata Manufacturing Co. and a pressurized air tank. Air supply unit 120 may be configured to supply a container 5 (illustrated in FIG. 1C) with air at a predetermined pressure.

Controller 130 may include a processor 132 and a memory 134 for storing thereon instructions to be executed by processor 132. Processor 132 may be a general purpose microcontroller. Memory 132 may include any non-volatile memory (e.g., flesh memory) configured to store thereon instructions for determining the amount of medication in a medication container or other instructions according to some embodiments of the invention.

Communication unit 140 may be configured to wirelessly communicate with external devices such as a mobile device 10 and an external processor 20. Mobile device 10 may be, for example, a smartphone, a tablet, a laptop, wireless gateway (e.g., at hospitals or clinics) and the like. External processor 20 may be any external processing and computation unit, for example, a cloud-based processing or computation service, a server, a central processing unit and the like. Communication unit 140 may communicate with external processor 20 either directly or via mobile device 10. Examples of the protocol used by communication unit 140 include but are not limited to Bluetooth, Bluetooth smart, BLE, Li-Fi, Wi-Fi, any IEEE 802.11 standard, ANT, ZigBee, near field communication (NFC), or any other standardized or proprietary communication protocol and/or frequency (band). Examples of near field communication includes but not limited to magnetic NFC, Radio-frequency identification (RFID). In some embodiments of the invention, components may communicate using sonic/ultrasonic technology, including but not limited to communication over audible or inaudible frequency.

Attachment sensor 150 may be or may include any sensor configured to sense the attachment or detachment of cap 100 to or from container 5. For example, attachment sensor 150 may include a button configured to be pressed against the walls of container 5 upon closure (as illustrated in FIG. 1B). In another example, attachment sensor may include: Optical sensor, capacitive sensor, accelerometer and the like. Attachment sensor 150 may sense the open and closure of cap 100 to container 5. Attachment sensor 150 may be further sense the degree of closure, meaning how tight the cap is closed.

User interface 160 may include any display or audio device that may allow the user to receive or provide information to or from controller 130. User interface 160 may include one or more lamps (e.g., LED lamps) for lightening icons, a small screen, one or more buttons, a speaker, a microphone and the like. User interface 160 may be included in the external side of cap housing 105, as illustrated in FIG. 1B.

Reference is now made to FIG. 1B, which is an illustration of some examples for components in a cap for a medication container according to some embodiments of the invention. Cap 100 may include a cap-shaped housing 105 for holding the various components of cap 100. Housing 105 may contain or otherwise hold an air supplying unit 120 (e.g., an air pump), controller 130 in communication with communication unit 140 (e.g., a Bluetooth device) and at least one pressure sensor 110 (e.g., a barometric pressure sensor). Housing 105 may further contain or otherwise hold a battery 115 and an attachment sensor 150 (e.g., a switch).

Cap 105 may further contain or otherwise hold one or more elements included in user interface 160. For example, user interface 160 may include one or more LED lamps 162 for lighting icons 164 on top of housing 105, as illustrated in FIG. 1C. User interface 160 may further include a button 166 illustrated in FIG. 1C.

Figure 2:
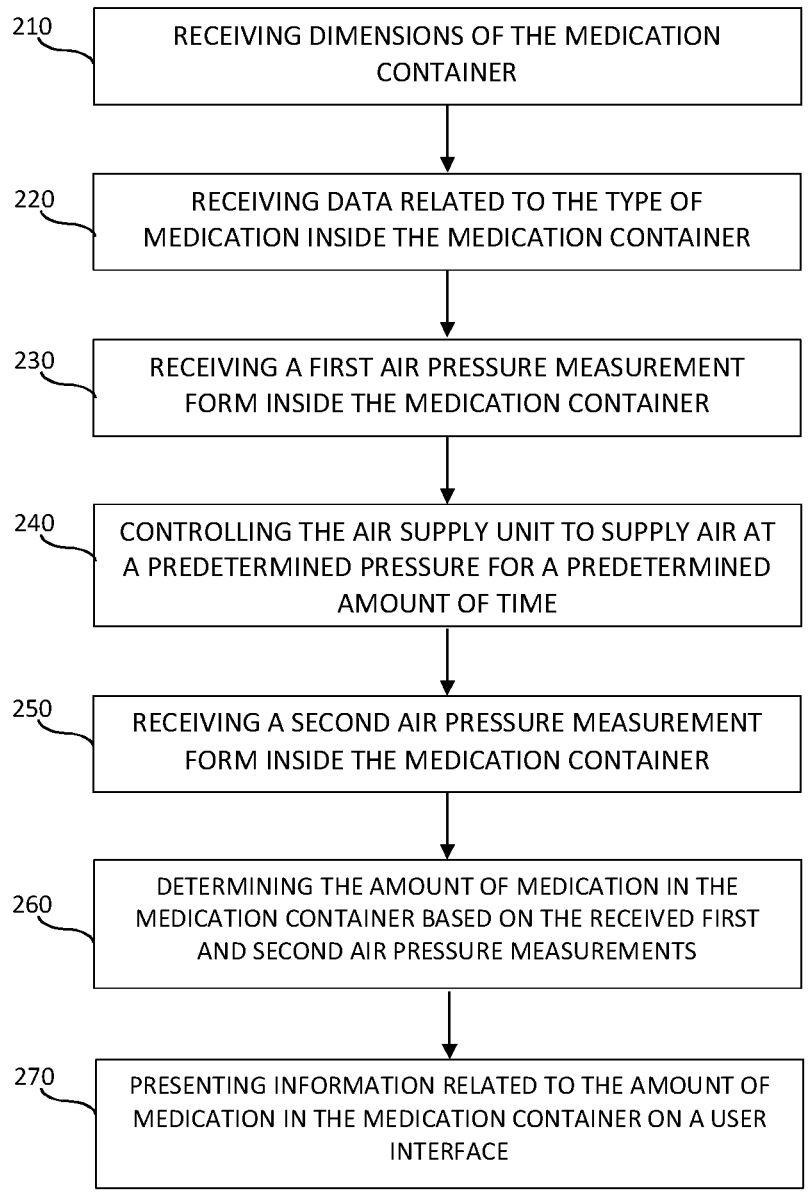
FIG. 2 is a flowchart of a method of determining the amount of medication in a medication container according to some embodiments of the invention.
Figure 3A:
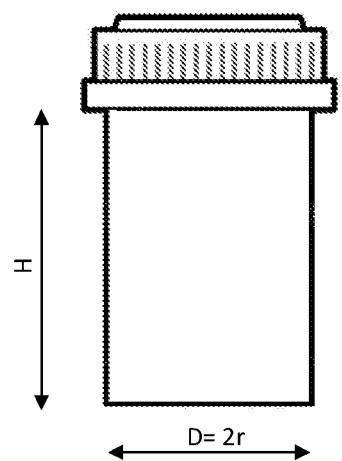
FIG. 3A is an illustration of an example of medication container according to some embodiments of the invention.

Reference is now made to FIG. 2, which is a flowchart of a method of determining the amount of medication in a medication container according to some embodiments of the invention. The method of FIG. 2 may be executed in whole or in part by processor 132, external processor 20, the processor of mobile device 10, or a combination thereof. In some embodiments of the invention, some of the steps in the method of FIG. 2 may performed by processor 132 and others may be performed by external processor 20 or the processor of mobile device 10. In step 210, dimensions of the medication container may be received. For example, the dimensions such as the height of the container H and the radius (r)/diameter (D)/side (L) of the container, as illustrated in FIG. 3A, may be received from a user interface. In some embodiments, a user may use buttons included in user interface 160 to enter the dimensions. Alternatively, the user may log into an application on user device 10 that enables the user to enter the dimensions of the medication container, which may be communicated to the cap processor 132. In some embodiments, the entered dimensions may be sent from mobile device 10 to cap 100 via communication unit 140. It will be clear that the communicated information may be the entered dimensions or a processed parameter, such as the container volume.

In some embodiments, the dimensions of the medication container may be automatically received from an external controller, such as external processor 20 or the processor of mobile device 10. In some embodiments, the external controller may be configured to receive one or more images of the container from a capturing device (e.g., a camera of mobile device 10) and may determine the dimensions of the medication container based on the received one or more images. The external controller may use any method of image analysis in order to analyze the images and extract the dimensions of the container from the images. Additionally or alternatively, the images may include an identification code (e.g., a barcode) to be recognized by the external controller and correlated to the dimensions of the medication container stored in a lookup table saved in a database.

Figure 3B:
FIG. 3B includes illustrations of an example for geometries of medication pills or capsules.

In step 240, data related to the type of medication inside the medication container may be received. In some embodiments, the data related to the type of medication may include at least one of: the state of the medication (e.g., pills, powder or syrup), dimension of pills at which the medication is given (as illustrated in FIG. 3B), an ID number, a serial number, FDA registration number and the like. In some embodiments, the data related to the type of medication may be received from a user interface, for example, user interface 160 or the user interface of mobile device 10. In some embodiments, the user may use buttons included in user interface 160 to enter the data. Alternatively, the user may log into an application on user device 10 that enables the user to enter the data.

In some embodiments, the data related to the type of medication may automatically be received from an external controller, such as external processor 20 or the processor of mobile device 10. In some embodiments, the external controller may be configured to receive one or more images of the medication and determine the data related to the type of medication based on the captured one or more images. The external controller may use any method of image analysis in order to analyze the images and extract the data related to the type of medication. For example, the external controller may determine if the medication is given in pills, powder or syrup form. If given in pills, the external controller may determine the shape and/or size of the pills, read identifying marking on the surface of the pills, and search for such characteristic information correlated with particular medications in a lookup table.

In step 230, a first air pressure measurement form inside medication container 5 may be received from at least one pressure sensor 110. In some embodiments, pressure sensor 110 may measure a first pressure level $P_1$ inside container 5. In some embodiments, the first pressure measurement may be taken only when cap 100 closes container 5. Processor 132 may further be configured to receive an indication that medication container has been opened and then closed from attachment sensor 150. In some embodiments, the first pressure measurement may be taken only after such indication has been received by processor 132.

In step 240, air supply unit 120 may be controlled to supply air at a predetermined pressure. In step 250, a second pressure measurement $P_2$ may be received from pressure sensor 110. In some embodiments, air supply unit 120 may supply air to container 5 until pressure $P_2$ has reached a desired level. Time $t_1$ may be the time taken for the pressure to reach from $P_1$ to $P_2$. In some embodiments, time $t_1$ may be predetermined.

In some embodiments, processor 132 may be configured to send the received first and second pressure measurements to the external processor for further processing. Additionally or alternatively, processor 132 may process the received first and second pressure measurements in order to determine amount of medication in the medication container.

In box 250, the amount of medication in the medication container may be determined based on the received first and second air pressure measurements, the dimensions of the medication container and the data related to the type of medication. In some embodiments, the amount of medication in the medication container may be determined by processor 132, external processor 20 or the processor of mobile device 10. In some embodiments, the received data related to the type of medication may include that the medication is given in pills having specific dimensions. Accordingly, determining the amount of medication may include determining the number of pills in the medication container. In some embodiments, the data related to the type of medication may include that the medication is given as powder or syrup. Accordingly, determining the amount of medication may include determining the volume of the medication in the container.

Processor 132, external processor 20 or the processor of mobile device 10 may calculate the amount of medication, for example, using the following or equivalent steps:
(1) calculating the volume $V_1$ of the container
(2) calculating the volume $V_2$ of each pill (when the medication is taken in pills)
(3a) calculating the volume $V_m$ of the medication in the container (when the medication is taken in powder or syrup) using equation I.

$$V_m = \frac{V_1(P_2 - P_1 - 1)}{P_1 + 1}. \quad \text{I}$$

(3b) calculating the number n of pills left in the container (when the medication is taken in pills) using equation II.

$$n = \frac{V_1(P_2 - P_1 - 1)}{V_2(P_1 + 1)}. \quad \text{II}$$

As will be understood by a person skilled in the art, steps 1-3 are given as an example only, and other equations may be used in order to calculate the amount of medication in the medication container.

In step 260, information related to the amount of medication in the container may be presented on a user interface. In some embodiments, the information related to the amount of medication may include at least one of: the amount of medication; an alert if the amount is below a predetermined level; an alert (e.g., a reminder) to take the medication after a predetermined amount of time from a previous reduction in the amount of medication determined by the controller, an alert not to take if the correct amount of reduction was determined on time, and the like. The information may be presented on small screen included in user interface 160, using lighted icons (e.g., icons 164) on cap 100, the screen of mobile device 10 and the like.

In some embodiments, the method may further include determining a first amount of medication in the medication container and initiating a time frame for determining a second amount of medication. The processor may further determine the second amount of medication in the medication container at the end of the time frame and send an alert to a user in the first amount is equal to the second amount or if the second amount is different from a predetermined second amount. For example, if no reduction in the amount was detected after the end of the time frame an alert may be send to the user device, for example, the icon on cap 100 may lighted with an icon of a pill or a message may be presented on mobile device 10 to remind him to take the medication. In yet another example, if the second amount of medication determined is different (higher or lower) than a predetermined second amount, an alert may be sent to user interface alerting a misuse of the medication, for example, the icon on cap 100 may lighted with an icon of a hand or a message may be sent and presented on user's device 10.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A cap for a medication container comprising:
   at least one pressure sensor;
   an air supplying unit; and
   a controller configured to:
      receive a first air pressure measurement from inside the medication container, from the at least one pressure sensor;
      control the air supply unit to supply air at a predetermined pressure for a predetermined amount of time;
      receive a second air pressure measurement from inside the medication container from the at least one pressure sensor; and
      perform an output operation using the first and second air pressure measurements.

2. The cap according to claim 1, wherein the controller is configured to perform an output operation selected from the group consisting of:

sending the received first and second air pressure measurements to an external processor, and determining the amount of medication in the medication container based on the received first and second air pressure measurements, dimensions of the medication container and data related to the type of medication.

3. The cap according to claim 1, wherein the controller is further configured to:
receive dimensions of the medication container; and
receive data related to the type of medication inside the medication container.

4. The cap according to claim 3, wherein the data related to the type of medication comprises dimension of pills at which the medication is given and wherein determining the amount of medication comprises determining the number of pills in the medication container.

5. The cap according to claim 3, wherein the data related to the type of medication comprises that the medication is in form of a powder or the medication is in the form of liquid and wherein determining the amount of medication comprises determining the volume of the medication in the container.

6. The cap according to claim 1, further comprising an attachment sensor, wherein the controller is further configured to:
receive an indication that medication container has been opened and then closed from the attachments sensor; and
receive the first air pressure measurement following receiving the indication.

7. The cap according to claim 1, wherein the cap is adapted to be fitted onto a medication container for storing at least one of the group consisting of: a medical drug, a dietary supplement, infant formula and vitamins.

8. The cap according to claim 1, wherein the air supply unit includes at least one of: an air pump and a pressurized air tank.

9. The cap according to claim 1, wherein the dimensions of the medication are received via a user interface in communication with the controller.

10. The cap according to claim 1, wherein the dimensions of the medication container are received from an external controller, and wherein the external controller is configured to:
receive one or more images of the container from a capturing device; and
determine the medication container based on the received one or more images.

11. The cap according to claim 1, wherein data related to the type of medication is received via a user interface in communication with the controller.

12. The cap according to claim 1, wherein data related to the type of medication is received from an external controller, and wherein the external controller is configured to:
receive one or more images of the medication; and
determine the data related to the type of medication based on the captured one or more images.

13. The cap according to claim 9, wherein the user interface is at least one of: a user interface included in the cap and a user interface included in a mobile device in communication with the controller.

14. The cap of claim 13, wherein the controller is further configured to:
present information related to the amount of medication in the medication container one the user interface.

15. The cap according to claim 13, wherein the information related to the amount of medication includes at least one of: the amount of medication; an alert if the amount is below a predetermined level and an alert to take the medication after a predetermined amount of time from a previous reduction in the amount of medication determined by the controller.

16. The cap according to claim 1, wherein the controller is further configured to:
determine a first amount of medication in the medication container;
initiate a time frame for determining a second amount of medication;
determine the second amount of medication in the medication container;
compare the first amount and the second amount; and
send an alert to the user interface based on the result of the comparison.

17. The cap according to claim 1, further comprising a communication unit configured to wirelessly communicate with external devices.

18. The cap according to claim 11, wherein the user interface is at least one of: a user interface included in the cap and a user interface included in a mobile device in communication with the controller.

19. The cap of claim 18, wherein the controller is further configured to:
present information related to the amount of medication in the medication container one the user interface.

20. The cap according to claim 18, wherein the information related to the amount of medication includes at least one of: the amount of medication; an alert if the amount is below a predetermined level and an alert to take the medication after a predetermined amount of time from a previous reduction in the amount of medication determined by the controller.

* * * * *